United States Patent
Schaedlich et al.

(10) Patent No.: US 6,475,802 B2
(45) Date of Patent: *Nov. 5, 2002

(54) APPARATUS FOR AND METHOD OF COLLECTING GASEOUS MERCURY AND DIFFERENTIATING BETWEEN DIFFERENT MERCURY COMPONENTS

(75) Inventors: Frank H. Schaedlich; Daniel R. Schneeberger, both of Toronto (CA)

(73) Assignee: Tekran Inc., Toronto (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/145,258

(22) Filed: Sep. 2, 1998

(65) Prior Publication Data

US 2001/0014478 A1 Aug. 16, 2001

(51) Int. Cl.[7] .......................... G01N 33/20; G01N 21/71
(52) U.S. Cl. .............................. 436/81; 422/50; 422/62; 422/78; 422/80; 422/81; 422/82.08; 422/82.09; 422/88; 436/73; 436/155; 436/158; 436/160; 436/177; 436/181; 436/182
(58) Field of Search .............................. 422/50, 62, 69, 422/78, 80, 81, 82.08, 82.09, 88; 73/23.31; 250/373; 436/73, 81, 155, 158, 160, 177, 181, 182

(56) References Cited

U.S. PATENT DOCUMENTS

| | | | | |
|---|---|---|---|---|
| 2,345,090 A | * | 3/1944 | Brace ........................... | 23/232 |
| 3,281,596 A | * | 10/1966 | Williston .................... | 250/43.5 |
| 3,640,624 A | * | 2/1972 | Anderson et al. ............. | 356/36 |
| 3,693,323 A | * | 9/1972 | Gant ............................. | 55/72 |
| 3,778,162 A | * | 12/1973 | Gant et al. ..................... | 356/51 |
| 3,933,431 A | | 1/1976 | Trujillo et al. ................. | 23/232 |
| 4,023,929 A | * | 5/1977 | Becker et al. .......... | 23/230 PC |
| 5,409,522 A | | 4/1995 | Durham et al. ................ | 75/670 |
| 5,597,535 A | | 1/1997 | Schaedlich et al. ........... | 422/88 |
| 5,660,795 A | | 8/1997 | Schaedlich et al. ........... | 422/88 |
| 5,679,957 A | * | 10/1997 | Durham et al. ............. | 250/373 |
| 5,750,992 A | | 5/1998 | Van Pelt et al. ............. | 250/372 |
| 5,879,948 A | * | 3/1999 | Van Pelt et al. ............... | 436/81 |

FOREIGN PATENT DOCUMENTS

| | | | | |
|---|---|---|---|---|
| DE | 43 21 454 | | 1/1995 | ............ G01N/1/28 |
| EP | 0 278 096 | | 8/1988 | .......... G01N/33/00 |
| FR | 2359412 | * | 3/1978 | |
| HU | 183070 | * | 7/1983 | |

OTHER PUBLICATIONS

E. N. Pollock Atomic Spectroscopy 1980, 1, 78–79.*
L. Yuan et al, Huanjing Huaxue 1993, 12, 231–236.*

(List continued on next page.)

Primary Examiner—Arlen Soderquist
(74) Attorney, Agent, or Firm—Bereskin & Parr

(57) ABSTRACT

A method and apparatus are provided for collecting a sample gaseous mercury, to differentiate between different gaseous mercury components. A quartz denuder module is provided having a coated extended surface for adsorbing reactive gaseous mercury. After collection of a sample, the coating it is heated to desorb the mercury as elemental gaseous mercury, which can then be detected and measured in conventional analyzer. During the sampling phase, as reactive gaseous mercury is removed from the sample flow in the denuder, the sample can then be passed to the analyzer for detection of elemental gaseous mercury. Where particulate mercury may be present, a filter trap can be provided downstream from the denuder. Separate steps can be provided for heating and pyrolysis of particulate mercury, for separate measurement in the analyzer. The pump module can be configured to a past the gas sample through scrubbers, to generate zero air as a flushing gas. The denuder can be mounted in separated module, so that it can be mounted in desired external location, remote from other instrumentation.

50 Claims, 3 Drawing Sheets

OTHER PUBLICATIONS

D. H. Sohn et al, Jpn. J. Toxicol. Environ. Health 1993, 39, 582–588.*

E. M. Prestbo et al, Water, Air, Soil Pollut. 1995, 80, 145–158.*

W. h. Schroeder et al, Water, Air, Soil Pollut. 1995, 80, 1227–1236.*

S. Wei et al, J. Environ. Sci. 1997, 9, 232–240.*

Z. Spiric et al, Am. Environ. Lab. 1998, 10, 16, 18–20.*

R. S. Braman et al, Environ. Sci. Technol. 1974, 8, 996–1003, Nov. 1974.*

W. H. Schroeder et al, Chemosphere 1987, 16, 183–199, Jan. 1987.*

A. C. W. Ng et al, Proc., Annu. Meet.–Air Waste Manage. Assoc. 1993, 86th, vol. 2, 93/TA/39.07, Jun. 1993.*

C. W. Brown et al, Proc., Annu. Meet.–Air Waste Manage. Assoc. 1996, 89th, 96–WA64A.01, Jun. 1996.*

J. A. Cooper et al, Proc., Annu. Meet.–Air Waste Manage. Assoc. 1996, 89th, 96–WA64A–06, Jun. 1996.*

R. B. Costanzo et al. Anal. CHem. 1988, 60, 826–829, Mar. 1988.*

K. Larjava et al. Chem. Abstr. 1993, 119, 255644f, Dec. 1993.*

J. Y. Lu et al. Anal. Chem. 1998, 70, 2403–2408, Jun. 1998.*

Larjava K. et al, "Measurement and control of mercury species in flue gases from liquid waste incineration", International Journal of Environmental Analytical Chemistry 1992, vol. 49, No. 1–2, 1992, pp. 73–85.

Lindberg, S.E., Stratton, W.J. "Atmospheric Mercury Speciation: Concentrations and Behavior of Reactive Gaseous Mercury in Ambient Air", Environ. Sci. Technol. 1998, 32, 49–57.

Xiao, Z. et al "Sampling and determination of gas phase divalent mercury in the air using a KCI coated denuder", Fresenius J. Anal Chem (1997) 358:386–391.

Larjava, Kari et al "Application of the Diffusion Screen Technique to the Determination of Gaseous Mercury and Mercury (II) Chloride in Flue Gases", Int. J. Environ. Anal. Chem. Appendix VI/1.

Larjava, K. et al "Development and Laboratory Investigations of a Denuder Sampling System for the Determination of Heavy Metal Species in FLue Gases at Elevated Temperatures", J. Environ. Anal. Chem. 38 (1990), pp. 31–45.

Larjava, Kari "On the measurement of volatile metal species at elevated temperatures", Technical Research Center of Finland ESPOO 1993, VTT Publications 137.

* cited by examiner

APPARATUS FOR AND METHOD OF COLLECTING GASEOUS MERCURY AND DIFFERENTIATING BETWEEN DIFFERENT MERCURY COMPONENTS

FIELD OF THE INVENTION

This invention relates to detecting and collecting mercury for air or other gas, and particularly is concerned with an apparatus for and a method of mercury speciation, which can differentiate between different components of gaseous mercury. More particularly the inventor is concerned with differentiating between the different components of mercury in ambient air and stack gas, namely gaseous elemental mercury vapour, gaseous ionic water soluble compounds of mercury, and particulate bound mercury.

BACKGROUND OF THE INVENTION

This invention is concerned with the detection of mercury and speciation of mercury, both in ambient air and in stack gases. There are three basic or largest components of gaseous or airborne mercury, namely: gaseous elemental mercury vapour, gaseous ionic water soluble compounds of mercury, and particulate bound mercury. Of the three basic components of gaseous or airborne mercury, the largest is gaseous elemental mercury $Hg^0$, i.e. non-ionized mercury vapour. Gaseous ionic water soluble compounds of mercury are generally known by the collective designations: reactive gaseous mercury (RGM), ionic mercury, or Hg (II), or $Hg^{2+}$; this class of compounds consists almost exclusively of mercury chloride, $HgCl_2$, since this compound is produced by combustion processes that have free chlorine present (for example, coal-fired power plants, waste incinerators, etc.). Particulate bound mercury comprises particles having mercury bound to them. In ambient air, the large majority of mercury in particulate form is contained in small particles <2.5 $\mu$m (microns) in diameter.

In background ambient air, elemental mercury generally comprises 90–98% of the total mercury; in stack gases, the proportions tend to be more equal. However, even for ambient air, the small reactive gaseous portion is extremely important, since it deposits locally and, being water soluble is a much larger local concern. Elemental mercury, which generally has a lifetime in the atmosphere 6–12 months, will often be deposited well away from its source. The RGM is present at very low concentration, e.g. 10–50 pg/m$^3$ so it must be preconcentrated before being analyzed.

There have been proposals in the art for measuring mercury and providing some degree of mercury speciation, i.e. measuring separately two or more components of mercury. Thus, one proposal is found in the paper entitled "Atmospheric Mercury Speciation: Concentrations and Behaviour of Reactive Gases, Mercury in Ambient Air" by S. E. Lindberg et al; *Environmental Science and Technology* 1998, Vol. 32, No. 1, pp. 49–57. There, the proposal is to use a high-flow refluxing mist chamber. This operates by drawing the sampled air through water disbursed as a fine aerosol. Water-soluble gases are adsorbed by the nebulised mist, and the droplets containing the scrubbed reactive gases of mercury coalesce on the surface of a hydrophobic membrane and then drain back into the chamber. The small solution volume required enables sampling times of the order of one hour to be used. Simultaneously, total gaseous mercury can be collected on old-coated sand adsorbers, but it should be noted that this technique collects all gaseous mercury, including the RGM. Particulate mercury is trapped by an external filter, which also traps some of the RGM. The mist chamber also has a particulate filter. The use of these filters tend to bias some of the RGM results low. The solutions from the mist chamber were analyzed by a wet chemistry technique, requiring reduction of the water soluble mercury ions to $Hg^0$ by stannous chloride. The mercury is purged from the mixture into a carrier gas using standard techniques and preconcentrated onto a gold cartridge. The total gaseous mercury was detected on the gold adsorber in known manner using cold vapour atomic fluorescence. What is noteworthy about this technique is that all the mercury species are not determined together, but require separate detection techniques, and moreover due to the wet chemistry techniques required to analyze the collected RGM, the technique is neither continuous nor suitable for automation.

A further proposal is found in the paper entitled "Sampling and Determination of Gas Phase Divalent Mercury in the Air using a KCl Coated Denuder" by Z. Xiao et al. in *Fresenius Journal of Analytic Chemistry* (1997) 358: 386–391. The technique proposed there used KCl denuders, formed by coating appropriately dimensioned glass tubes with KCl from a saturated KCl solution. The experiments reported show that gaseous elemental mercury ($Hg^0$), simply passes through the denuders without being adsorbed, and apart from some apparent system errors, 100% "passage" of elemental mercury vapour was reported. For field sampling, two lines were set up, one for collecting gaseous $Hg^{2+}$ species using a KCl denuder and the other for conventional sampling of total gaseous mercury. It is noted that the effective recovery and analysis of the collected mercury from a denuder is an important step. Here, the mercury is recovered by HCl extraction followed by CVAFS (Cooled Vapour Atomic Fluorescent Spectroscopy). Again, such a technique is complex, and is not suited for continuous monitoring and cannot readily be automated.

A further series of developments and experiments have been reported by K. Larjava and others as follows:

"Development and Laboratory Investigations of a Denuder Sampling System for the Determination of Heavy Metal Species in Flue Gases at Elevated Temperatures" by K. Larjava et al, *International Journal of Environmental & Analytical Chemistry*, 38 (1990), pp. 31–45;

Application of the Diffusion Screen Technique to the Determination of Gaseous Mercury and Mercury (II) Chloride in Flue Gases by K. Larjava et al., accepted for publication in the *International Journal of Environmental & Analytical Chemistry;* and On the measurement of Volatile Metal Species at Elevated Temperatures by K. Larjava—Dissertation for the degree of Doctor of Technology to be presented at Helsinki University of Technology on May 21, 1993.

Here again, there is a disclosure of the use of annular denuder tubes coated with potassium chloride for collecting mercury species. These papers focus on the basic research and do not teach any complete, functioning instrument, capable of speciating mercury vapour.

Accordingly, known techniques suffer from a number of disadvantages. Commonly, they require a denuder collector or the like to be extracted from the equipment and analyzed using wet chemical techniques. Such a method is not suited to continuous monitoring, nor to an automated system.

A further problem with detection of RGM, which has not been fully identified in the art, is that common ionic mercury compounds have a strong affinity to adsorb onto a wide variety of surfaces. In this sense, ionic mercury is "sticky", and extremely difficult to handle. Bearing in mind that the problem is to detect very low levels of ionic mercury, the small amount present readily adsorbs onto surfaces of tubing, valves and other fittings distorting any reading made.

Another problem with the determination of RGM is that it is very difficult to separate the RGM from the particulate mercury. Previously, this has been extremely difficult, as one known technique is to provide a particulate filter upstream of a denuder, to filter out the particulate mercury. However, due to the characteristics of reactive gaseous mercury, some fraction of it would collect on the particulate filters, leading to a false low reading for the measured amount of reactive gaseous mercury.

SUMMARY OF THE INVENTION

The present inventors have realized that, when measuring mercury vapour, including reactive gaseous mercury, it is necessary to take extra steps, to ensure that the reactive gaseous mercury does not collect onto surfaces before reaching a detection device intended to detect its presence.

Additionally, the present invention is directed to a technique which will allow continuous and automated measurement of mercury vapour, including speciating of the three principal components, namely gaseous elemental mercury vapour, gaseous ionic water soluble compounds of mercury or reactive gaseous mercury, and particulate bound mercury. More particularly, the present invention proposes detecting these three elements in a particular sequence, using appropriate detection techniques which will not interfere with one another.

The present invention is also directed to providing an improvement in the analysis of samples collected in denuders or other adsorption units coated with potassium chloride, or other suitable coating for detecting mercury. More specifically, the present invention is intended to avoid the use of complex wet chemistry techniques, which are not suitable to automated operation.

In background ambient air, elemental mercury generally comprises 90–98% of the total mercury. However, the small remaining reactive portion is extremely important, since it deposits locally and, being water soluble is a much larger local concern than elemental mercury, which generally has a lifetime in the atmosphere of 6–12 months.

The reactive gaseous mercury is present in such low concentrations (the values are typically 10–50 pg/m$^3$). It must be preconcentrated before being analyzed. The present invention provides a device that can be used as a front end or interface for a conventional mercury analyzer, through which air can be passed at a high flow rate, typically 10 litres per minute, for a varied period of time, typically 40 minutes to 2 hours to effect this preconcentration.

The present invention has numerous advantages over the prior art. Where a regeneratable particulate filter is provided, then the three principal components or gaseous mercury can be separated and analyzed. This can be carried out continuously and in an automated fashion. The present invention in preferred embodiments, provides a regeneratable particle filter located downstream of a denuder, so as not to interfere with collection of reactive gaseous mercury in the denuder.

In accordance with a first aspect of the present invention, there is provided a detection module, for detecting airborne reactive gaseous mercury and for use with mercury analysis equipment, the detection module comprising:

an adsorption unit having an extended transfer surface and a coating on the transfer surface for adsorbing reactive gaseous mercury from a gas passing through the adsorption unit, the adsorption unit having an adsorption unit inlet opening directly to a gas sample containing reactive gaseous mercury and an adsorption unit outlet for connection to a pump means, for drawing the gas sample through the adsorption unit;

a first inlet for a flushing gas, substantially free of mercury vapour, for flushing out of the adsorption unit and connectable to the adsorption unit inlet;

a heating means for heating the adsorption unit to a suitable desorption temperature higher than an adsorption temperature to cause reactive gaseous mercury adsorbed onto the coating to be released as gaseous elemental mercury vapour, for measurement; and a temperature controller for controlling the heating means, whereby the adsorption unit can be maintained at the adsorption temperature for adsorption of the reactive gaseous mercury and, at the desorption temperature for desorption of elemental mercury.

The adsorption unit can be any suitable device which provides an extended surface for adsorption of RGM, and capable of releasing mercury by heating. A denuder configuration is preferred where particulate mercury is present, as this permits the particulate mercury to pass through, for collection in a filter. For other uses, particularly where particulate mercury is not a concern, other adsorption unit configurations can be provided, e.g. packed quartz chips.

Preferably, the heating means includes a first heating element located around the denuder and a first heating controller connected to the first heating element, the first heating controller being capable of regulating the temperature of the first heating element to a first temperature at which the denuder functions to adsorb the reactive gaseous mercury, and to a second, elevated temperature at which reactive gaseous mercury compounds adsorbed on the denuder break down and release mercury as gaseous elemental mercury vapour.

The apparatus advantageously includes a detection module housing, in which the denuder is mounted with the denuder inlet extending out of the detection module housing, and wherein the heating means includes a second heating element located around the denuder inlet and a second heater controller connected to the second heating element, for maintaining the denuder inlet at a set temperature. The heating means can include a third heating element within the detection module housing for heating the housing and a third heating element controller for control thereof.

Preferably, at least one fan is provided for cooling the denuder, and more preferably, there are a first fan for cooling the denuder and a second fan for blowing air through the detection module housing for cooling thereof.

To handle particulate mercury, a filter pack can be provided, preferably comprising a filter material capable of being subjected to elevated temperature to release of mercury vapour to regenerate the filter pack, whereby particulate mercury can be collected in the particulate filter pack and the mercury can be released as elemental mercury vapour by heating of the filter material.

The apparatus can include, independably of or in addition to other aspects of the invention, an inlet T-shaped connector connected to the denuder inlet, the inlet T-shaped connector providing a straight through connection for a gas sample and a side connection connected to the first inlet for supply of flushing gas. This is a significant aspect of the present invention as it eliminates the need for a valve at the denuder inlet. It is to be noted that the connector need not be T-shaped; the key concept is to use the flushing gas flow to close off the denuder inlet to the exterior and for this purpose the inlet can have various shapes provided it includes an opening for the sample gas and an opening for the flushing gas.

Conveniently, a first valve is provided having a first connection port connected to the first inlet, a first valve outlet and a second valve outlet, with the side connection of the T-shaped connection connected to second valve outlet, and a flow restrictor connected to the first valve outlet, whereby the first valve can selectively connect the first inlet to either the flow restrictor for enabling a restricted flow of flushing gas to vent to atmosphere or to the denuder through the T-shaped connection for supply of flushing gas.

Preferably, the denuder is of the annular type and the coating comprises a salt, or a combination of salts, more preferably potassium chloride. The denuder is preferably formed from quartz glass.

Another aspect of the present invention provides an apparatus for the detection of reactive gaseous mercury, the apparatus comprising:

(1) an adsorption unit having an extended surface and a coating of ionic salt on the extended surface for adsorbing reactive gaseous mercury, the adsorption unit having an adsorption unit inlet opening directly to a sample gas and an adsorption unit outlet;

(2) a heating means for heating the adsorption unit to a suitable desorption temperature higher than an adsorption temperature to cause gaseous reactive mercury adsorbed on the coating to be desorbed and vaporized as elemental mercury;

(3) a temperature controller for controlling the heating means, whereby the adsorption unit can be maintained at the adsorption temperature for adsorption of the reactive gaseous mercury and, at the desorption temperature for desorption;

(4) a pump means connected to the adsorption unit outlet for drawing a gas sample through the adsorption unit; and (5) a flushing gas supply means for supply of a flushing gas and connectable to the adsorption unit inlet, for passing flushing gas through the adsorption unit, whereby in use, a sample gas is drawn through the adsorption unit by the pump means in a sampling phase and reactive gaseous mercury is adsorbed onto the coating of the adsorption unit, and in a desorption phase, the heating means is actuated and flushing gas is passed through the adsorption unit from the adsorption unit inlet to the adsorption unit outlet so that adsorbed reactive gaseous mercury is desorbed, vaporized and entrained in the flushing gas flow.

Conveniently, the flushing gas supply means is integral with the pump means and is connected to the denuder inlet by a flushing gas supply line.

The pump means can be connected to the denuder outlet by a sample line, and the sample line then includes a branch connection port for connection to an analyzer.

Another aspect of the present invention provides an apparatus for use in monitoring stack gases. The apparatus then includes a dilution unit having an inlet for stack gases, an outlet connected to the denuder outlet, and an inlet for dilution air. The dilution air inlet is preferably connected to the flushing gas supply means. Such an apparatus can include an acid gas scrubber connected between the pump means and the denuder outlet for scrubbing acid gas from the gas flow.

Another aspect of the present invention provides a method for determining the quantity of reactive gaseous mercury in a gas, the method comprising the steps of:

(1) passing a gas sample through an adsorption unit having an adsorption unit inlet opening directly to a gas sample and an adsorption unit outlet, said adsorption unit having an extended surface provided with a coating for adsorbing reactive gaseous mercury and being maintained at a suitable adsorption temperature above ambient temperature of the gas sample to prevent condensation of water vapour during adsorption;

(2) after a known quantity of gas has been passed through the adsorption unit, terminating supply of the sampled gas, and passing a flushing gas through the adsorption unit; and (3) while passing the flushing gas through the adsorption unit, heating the adsorption unit to a suitable desorption temperature higher than the desorption temperature to cause desorption of reactive gaseous mercury compounds as gaseous elemental mercury vapour for entrainment in the flushing gas, and passing the flushing gas with the entrained gaseous elemental mercury vapour to a mercury analyzer.

Preferably, the denuder in step (3) is heated to a temperature in the range of 500° C.

Preferably, the method includes passing a portion of the gas sample that has passed through the denuder to a mercury analyzer, for determination of the level of gaseous elemental mercury vapour in the gas sample.

Where particulate mercury might be present, the method can include filtering out particles containing particulate mercury from the gas sample, downstream from the denuder. This is preferably done with a regeneratable filter pack, and prior to step (3), the regeneratable filter pack is heated to a temperature whereby particulate mercury is desorbed from the regeneratable filter pack as gaseous elemental mercury vapour, and that gaseous elemental mercury vapour in is then entrained in the flushing gas flow, for determination of the level of particulate bound mercury.

In another aspect of the present invention an extract from stack gases is taken, and, prior to step (1), the extract is diluted with a flushing gas, substantially free of mercury and having a low relative humidity, to dilute the stack gas extract and to form the gas sample with a reduced relative humidity.

DESCRIPTION OF THE DRAWING FIGURES

For a better understanding of the present invention, and to show more clearly how it may be carried into effect, reference will now be made, by way of example, to the accompanying drawings, in which.

DETAILED DESCRIPTION OF THE INVENTION

Figure 1:
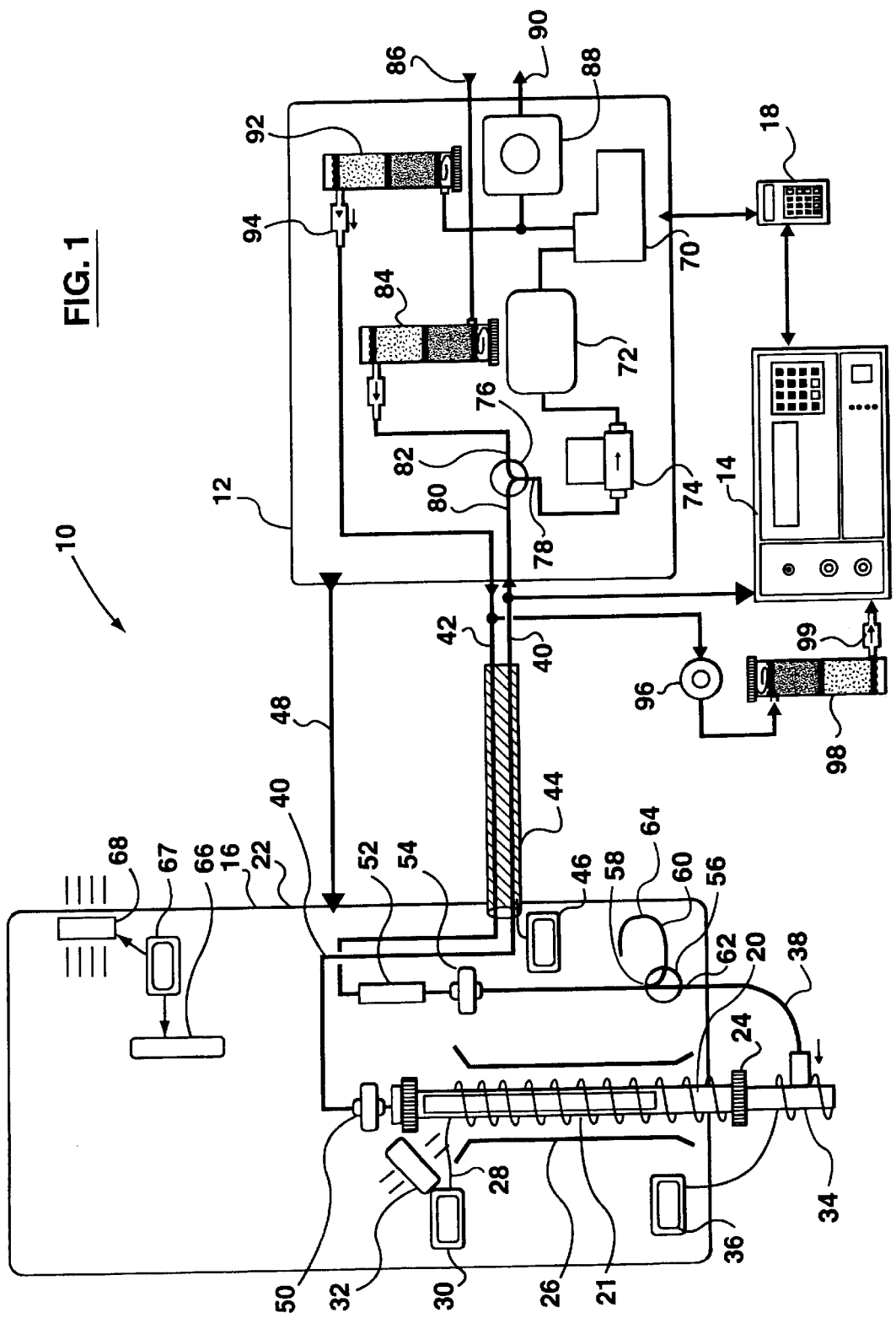
FIG. 1 is a schematic view of a first embodiment of an apparatus in accordance with the present invention.

Referring first to FIG. 1, an apparatus in accordance with the present invention is generally designated by the reference 10. The apparatus 10 comprises three main units and a controller. The main units are a pump module 12, an analyzer 14, and in accordance with the present invention a denuder or detection module 16. The pump module 12 and analyzer 14 are connected to a controller 18, which preferably is a digital controller. The analyzer 14 is preferably a model 2537A analyzer manufactured by Tekran Inc. of Toronto, Ontario, the assignee of the present invention. Similarly, the pump module 12 and controller 18 are preferably a model 1130 Speciation Unit, also manufactured by Tekran Inc. These components 12, 14 and 18 are also generally in accordance with assignee's earlier U.S. Pat. Nos. 5,597,535 and 5,660,795.

The construction and operation of the denuder module 16 is based on a major discovery made by the inventors of the present invention. Conventionally, it has been thought that, after collecting reactive gaseous mercury in potassium chloride in a denuder, it was necessary to use some wet chemistry techniques to extract the potassium chloride with the mercury and determine the amount of mercury present. What the present inventors have discovered is that the potassium chloride coating can be heated to a high temperature, and it can be caused to release the mercury as mercury vapour. Further, the potassium chloride coating releases the adsorbed reactive mercury as elemental mercury. This release of mercury as elemental mercury is extremely important, as elemental mercury passes through sampling lines easily without any tendency to adsorb or condense. Moreover, elemental mercury can be readily analyzed and quantified using the model 2537A analyzer, or other conventional analyzing equipment. Mercury chloride on the other hand, through its tendency to be "sticky", is extremely difficult to pass through lines, and there are references in the art suggesting that it can take hours to completely pass mercury chloride through lines and flush out the lines.

Accordingly, in accordance with the present invention, the active sampling element in the denuder or detection module 16, for speciating the front end, is a coated thermally regeneratable quartz denuder 20. The denuder 20 has been specially designed so that it can be analyzed by thermal desorption and regenerated many hundreds of times before requiring recoating. The denuder is made of quartz glass so as to allow repeated heating to temperatures in excess of 500° C. The adsorbing surfaces are etched to roughen them to allow the coating to adhere despite the rigours of repeated thermal cycling. A detailed discussion of the structure of quartz denuder 20 is provided later in this disclosure, with reference to FIG. 3.

It is to be appreciated that, in accordance with the present invention, the essential requirement for the module 16 is to provide an adsorption unit extended surface, with a suitable coating, to enable gaseous mercury to be collected at a desired efficiency. Thus, a straight denuder or quartz chips packed into a cartridge could be used as the adsorption unit. Whatever the structure of the adsorption unit, the coating should be one capable of releasing mercury, preferably in elemental form, by simple heating. The inventors have discovered that ionic salts, such as KCl, NaCl or a KCl/soda lime mixture, give satisfactory performance, but any suitable coating could be used.

The denuder module 16 includes a housing 22, and a mounting arrangement 24 for the quartz denuder 20. The denuder 20 slides into a tight fitting tube 21 containing the heating element and temperature sensor. The tight fit is required to provide efficient heat transfer from the heater to the denuder. A generally tubular element 26 defines a duct around the quartz denuder 20. A heating element 28 is disposed helically, so as to be located around the quartz denuder 20, and is connected to a suitable heater controller 30. A fan 32 is provided for blowing ambient air through the tubular element 26 for cooling the denuder 20.

Externally, the quartz denuder 20 is provided with a heated inlet 34 connected to a respective heater controller 36. The heater controller 36 and also the heater controller 30 are dual point controllers. The controller 30 allows separate temperatures to maintained during different parts of the analytical cycle. During the sampling phase, the denuder 20 may be maintained slightly above ambient temperatures (eg: +50° C.) by heater controller 30 so as to prevent high ambient humidity levels from dissolving hygroscopic coatings through the absorption of moisture. During the heating phase, controller 30 keeps the temperature of the denuder 20 at typically 500° C.

The second dual setpoint controller 36 allows the upstream sampling components to he heated to an elevated temperature during the desorption phase of the measurement cycle. This allows any RGM that was adsorbed onto the sampling components to be cleaned off, thus reducing carry over from one cycle to the next.

The inlet 34 comprises a T-shaped connector (209 in FIG. 3), providing a connection to a zero air supply line 38 for the supply of "zero" air, i.e. air that has been filtered and had the mercury level reduced to below 0.02 ng/m$^3$. More generally this can be referred to as a flushing line for a suitable flushing gas, i.e. a gas other than air could be used. The inlet of the denuder may optionally be fitted with a series of interchangeable particulate sizing devices of conventional design. These "impactors": are well known in the art and provide a convoluted flow path that traps particles of greater than the designed cutoff size while passing smaller particles. This device allows the particulate size fraction being monitored to be easily selected. Unlike filter membranes, impactors do not require the sample to actually pass through the separating element.

Another important aspect of the present invention is the mounting and location of the denuder 20. Bearing in mind the strong tendency for reactive gaseous mercury to stick to various surfaces, the denuder 20 is provided in its own module and is provided with an inlet that opens directly to ambient atmosphere or other gas whose mercury content is to be measured. In other words, there are no intervening carrier or transport lines, through which air or other gas has to pass before reaching the quartz denuder 20.

Extending from the top of the quartz denuder 20 is a sample line 40 which extends to the pump module 12. Extending from the pump module 12 to the denuder module 16 is a zero air line 42 connected to the zero air line 38 within the detection module 16. The two lines 40, 42 are encased in a common heated casing 44, connected to a heated line controller 46, for regulating the temperature of these two lines. The pump module 12 also includes control line connections 48 to the denuder module 16, for control signals originating from the controller 18.

A particulate filter pack 50 is provided immediately above the quartz denuder 20, in the sample line 40. According to a further significant aspect of the present invention, this filter pack 50 is preferably a regeneratable filter pack, which includes a heater and a pyrolyser, for desorption and pyrolysis of mercury or mercury compounds present, to generate elemental mercury for detection in the analyzer 14, as detailed below. The configuration of the filter pack heater and pyrolyser are detailed further in FIG. 2 in relation to the stack version of the device.

The zero air line 42 passes into the denuder module 16, and through a final zero filter 52. The line 42 then extends through a second particulate filter pack 54 and then through a first valve 56. The first valve 56 is a two way valve having an inlet or first connection port 58, which can be connected through to a first outlet 60 or a second outlet 62. The first outlet 60 is connected to a flow restrictor 64, for providing a restricted flow of 100 mL per minute, for reasons detailed below. The second outlet 62 is connected to the T-shaped connection.

Within the pump module 12, there is a sample pump 70 connected to a buffer tank 72, which in turn is connected to a mass flow meter 74.

A second valve 76 has a second, common connection port 78 connected to the mass flow meter 74 and first and second inlet ports 80 and 82. The first inlet port 80 is connected to the sample line 40, while the second inlet port 82 is connected to a first stage scrubber for the zero air line, indicated at 84. This first stage scrubber 84 in turn has an inlet connected to an air inlet 86 for ambient air.

The outlet of the pump 70 is connected to a back pressure regulation valve 88, which in turn is connected to a vent 90 opening to atmosphere. The back pressure regulating the valve is set to generate a back pressure of approximately 1 psi. The pump outlet is also connected to a second stage mercury scrubber 92, having an outlet connected by a particulate filter 94 to the zero air line 42.

A connection is provided from the zero air line 42 through the pressure regulator 96 to a third scrubber 98. The zero line then passes through a fine particulate filter 99 into the analyzer 14. The zero air thus provided is used in clean and calibration cycles within the analyzer 14.

The denuder or detection module 16 has four independent temperature controllers, each capable of maintaining two set points. For the quartz denuder 20, the heater controller 30 can be set to different temperatures. Typically, it can be set to 50° C. for the sampling phase, so as to eliminate condensation problems; note that a temperature above 85° C. during sampling can lead to an erroneous reduction in the amount mercury adsorbed in the denuder 20 and hence detected. During the desorption phase, it would typically be set to a temperature 500° C. For the external temperature control, the heater controller 36 for the heated inlet 34, during the sampling phase, can typically be set to a temperature of 50° C. During the desorption phase, it can be set to a slight higher temperature typically 90° C. The heated casing 44 for the gas lines can typically be maintained at temperature of 50° C. A controller 67 for the case heater 66 also serves to control the actuation of fan 68. Typically, this would be given two fairly close set points, one to activate the fan and the other to activate the heater; for example, a low temperature setting of 38° C. can be used to activate the case or housing heater 66, and a high temperature setting of 40° C. to activate the fan 68, to maintain denuder housing 22 within desired limits.

The sample pump 70 is controlled by a closed loop controller that senses the pump flow through the mass flow meter 74 and adjusts the pump appropriately, to maintain the desired flow rate; flow through the analyzer 14 is controlled to a desired constant value. The pump 70 and mass flow meter 74 have dual set points, one for sampling and one for desorption phase typically 8.5 l/m and 4 l/m.

The lines 42, 44 between the pump module 16 and denuder or collection module 16 can be up to 25 feet long, and the heater 44 is provided to prevent condensation and to ensure that the lines do not have the opportunity to adsorb significant mercury. The heater controller 46 for the line heater 44 is located in the denuder module 16.

While a model 2537A analyzer is used, it must be set so that it will not automatically recalabrate itself. Routine timed recalibrations are controlled by the controller 18, which will schedule recalibrations in the analyzer 14 after a set number of desorption cycles, the set number of cycles being programable.

A significant aspect of the present invention is that the denuder or detection module 16 may be located outside.

It is preferred for the denuder module 16 to mounted vertically, with the denuder inlet pointing down. It is essential that any materials that can out gas mercury be kept well away from the inlet to the quartz denuder 20. The mounting height above ground must be sufficient to prevent any wind blown "dust", and any particulate matter from being drawn into the quartz denuder 20.

In use, the apparatus 10 is operated in distinct sampling and desorption or analysis phases. In the sampling phase, the denuder module 16 is operated to capture reactive gaseous mercury with high efficiency, and in the desorption or analysis phase the denuder is thermally desorbed, for the mercury to be analyzed in the analyzer 14. While the sampling cycles are taking place, the analyzer 14 is performing separate analysis and desorption cycles for determining gaseous elemental mercury vapour, as detailed in the assignee's earlier U.S. Pat. No. 5,597,535. This is carried out in the sampling phase of the denuder module 16 as detailed below.

During the sampling phase, the first and second valves 56 and 76 are in what are considered to be "off" positions; thus, the inlet or first connection port 58 of the first valve 56 is connected to the first valve outlet 60, and the second connection port 78 of the second valve 76 is connected to its first inlet port 80.

Consequently, the flow through the sample line 40 is drawn through the mass flow meter 74 and the tank 72 by the pump 70. The pump in turn discharges the air through to the zero air line 42, through the second stage scrubber 92, with any excess air being vented at 90. Most of the air would be vented, with only a small flow of zero air being permitted through the restrictor 64, this is to maintain a steady, forward flow of zero air, to keep all zero air components purged and free of mercury.

The analyzer 14, where this is the model 2537A analyzer, samples at 1.5 litres per minute for its normal operation. In addition, a larger flow is taken to meet the requirement of the denuder module 16. The mass flow meter 74 is set to a flow of 8.5 l/m, so that the total flow through the quartz denuder 20 and the denuder module 16 is 10 l/m. In this sampling phase, the analyzer 14, reports a pure elemental mercury concentration, since the reactive gaseous component is being removed by the quartz denuder 20.

When the sampling period is complete, the denuder is thermally desorbed. This heating process releases the reactive gaseous mercury retained on the potassium chloride coating of the denuder. Further, as noted above, the heating process liberates the mercury in the form of elemental or non-ionized mercury that travels easily through sampling lines and filters, and of significance, in a form that can be analyzed by the selected analyzer 14, i.e. the model 2537A analyzer. At the end of the analysis cycle, the quartz denuder 20 is clean and ready for a fresh cycle.

The basic desorption cycle or phase consists of three periods, as detailed below. In the event that becomes necessary to break one or more of the periods into smaller steps for example, to allow heaters, fans, flow rates etc. to be modified during each period, the controller 18 is preferably capable of implementing a maximum of six periods during the desorption phase. The times for the periods are user programmable and will normally be selected to coincide with the cycle times for the selected analyzer 14. The values given below are estimated durations for reference only. During desorption, both valves 56 and 76 are actuated. The first valve 56 then has its inlet or first connection port 58 connected to the second valve outlet 62 (this valve being shown schematically), and the second valve 76 has its second connection port 78 connected to the second inlet port 82.

Actuation of the first valve 56 causes zero air to be introduced into the bottom of the quartz denuder 20, for a first flushing period. This is places all of the ambient air in the system, eventually causing the nalyzer 14 to report a very low background reading that corresponds to residual mercury levels in the system. This flow rate is set at 4 l/m, with 1.5 l/m passing upwards through the quartz unit 20, as determined by the sample requirements of the analyzer 14. Flushing will usually take 3 to 10 minutes. The extra 2.5 l/m flows out of the inlet 34, and prevents contamination from ambient air, without requiring any valve in the inlet itself.

The next period is a heating period, which usually takes 5 to 10 minutes. The denuder is heated to a high programmable temperature in the range of 500° C. The desorption period is not instantaneous, as is the case with mercury on gold. However, the assignee has found that the quartz denuder 20 can usually be fully desorbed within one or two measurement cycles. The cycle (analysis) time of the Model 2537A is typically fixed at 5 min and cannot be changed on a cycle by cycle basis. Thus two heating cycles are currently required to get all of the RGM off the denuder 20, the two values are added to give the total RGM value. In subsequent versions, with a smaller denuder, higher wattage heaters to heat faster, different coating, higher temperature, etc., it is anticipated that heating period could be reduced substantially. Typically, over 95% of the mercury loading is released on the first cycle, but for maximum accuracy, the mercury readings from all of the desorption cycles should be added to obtain an accurate RGM value.

Finally, there is a cooling period, usually lasting from 3 to 10 minutes. In this period, the quartz denuder 20 is cooled, by turning off the heating element 28, and cooling the denuder 20 with the fan 32. This cooling is enhanced by internal cooling with zero air. After the quartz denuder 20 has cooled sufficiently, a new sampling cycle may begin.

The housing 22 is a weatherproof, temperature controlled enclosure, which eliminates the need for a sampling manifold or sampling line. The denuder module 16 requires a fair amount of power. In known manner, it is equipped with its own power cord. At least for use in North America, it should be powered from a dedicated 120 volt AC, 15 ampere branch circuit, and should be connected to a supply with a three wire grounded cord. As a preferred safety feature, all power should be routed through a ground fault interrupter module.

The quartz denuder 20 in trials by the assignee has been found to last for several weeks of continuous one hour cycles before requiring recoating. The recoating process is outlined below, and generally follows that used for other types of ambient air denuders. For the measurement of particulate, as noted above, the filter pack 50 could be provided as a regeneratable filter pack, including a heater and pyrolyser, as detailed below in relation to FIG. 2.

During sampling, RGM is trapped or captured by the quartz denuder 20. HgP or particulate mercury is trapped or collected in the filter pack 50, while elemental gaseous mercury passes through to the analyzer 14. During the sampling phase, the analyzer 14 reports a pure elemental mercury value.

To measure the amount of particulate mercury captured, the valves 56 and 76 are actuated as for desorption of the RGM. However, in this case, the quartz denuder module 16 is not initially heated. Zero air then flows through the denuder module 16, without heating, and then through the filter pack 50.

The pyrolyser within the filter pack 50 is heated first, so as to preheat this to a desired temperature. This is to ensure that any mercury released from the filter itself, which may still be in a compound form, is pyrolysed and converted to elemental mercury.

Then, the heater surrounding the particulate filter is actuated or turned on. This will release all mercury compounds from the filter 50. Before the filter reaches the maximum temperature, some mercury will be released in compound form, rather than in elemental form, and it is for this reason that the pyrolyser is preheated first, to ensure that all mercury that flows downstream through the sample line to the analyzer 14 is in elemental form. The analyzer 14, in known manner, will then determine the quantity of mercury that had been captured by the particulate filter pack 50.

As the fitter 50 is heated in air, the oxygen present will cause trapped carbon based particles to oxidize to carbon dioxide, helping to keep surfaces clean.

Once the particulate filter pack 50 has been fully desorbed, then, the amount of mercury accumulated on the quartz denuder 20 can be measured. The heaters for the particulate filter pack 50 are kept actuated. With heating of the quartz denuder 20, the mercury captured therein will pass transparently through the heated particulate filter pack 50 to the analyzer 14 for measurement.

Finally, as for sampling with just the quartz denuder 20, all heaters are turned off and cooled as quickly as possible. The valves 56 and 76 are returned to their normal position and a new sampling cycle begins.

Figure 2:
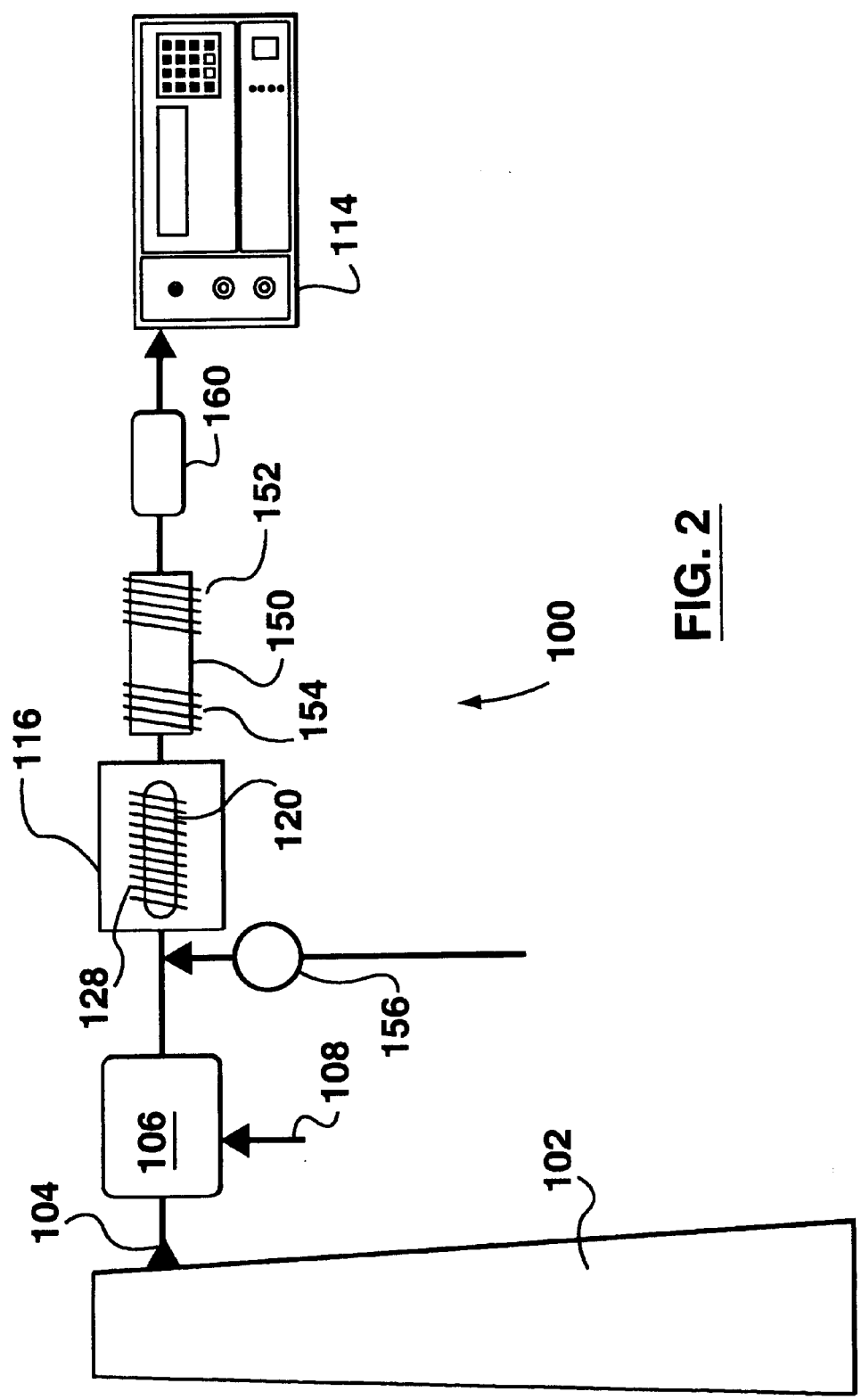
FIG. 2 is a schematic view of a second embodiment of an apparatus in accordance with the present invention, for monitoring stack gases.

Reference will now be made to FIG. 2, which shows a second embodiment 100 of the apparatus of the present invention. This is intended for use in monitoring stack gases, and a typical industrial stack is shown schematically at 102. A sample of stack gas is drawn off at 104 and passed to a dilution unit 106. Zero or dilution air is supplied to the dilution unit 106 at 108. This is for two reasons. Firstly, stack gases have very high concentration is of mercury compared to ambient air, and hence dilution can prevent overload of the analyzer 14. Additionally, dilution reduces the relative humidity, and the concentration of potential interferents, so as to reduce the possibility of a unwanted condensation of water vapour in the system and to prolong the lifetime of the quartz denuder here indicated at 120.

In the second embodiment 100, as large sample volumes are not required, the quartz denuder 120 can be smaller. This facilitates rapid heating and cooling, allowing quicker cycle times and faster measurement cycles. It can be noted that for stack gases, the ratio of elemental to reactive mercury can vary over a wide range which is generally more equal or centred, around a 50:50 ratio, as compared to relative concentrations in ambient air. The denuder 120 has a heater 128.

The dilution unit 106 has an outlet connected to the quartz denuder collection module, here denoted 116. The inlet 108 is provided upstream of the quartz denuder for zero air, for desorption.

The quartz denuder collection module 116 has a connection through a first valve 156 for zero air, and is connected through a regeneratable particulate filter trap indicated at 150, which is connected to an acid gas scrubber 160. The scrubber 160 is intended to remove any acid gas components from the flow, to prevent these flowing through to the analyzer and possibly damaging the analyzer. The outlet of the acid gas scrubber 160 is connected to the analyzer 114, which again can be a model 2537A analyzer.

In use, this second embodiment 100 is operated in much the same manner as the first embodiment or apparatus 10. Thus, during a sampling phase, a sample is taken off continuously from the stack 102. This sample is diluted with zero air and flows through the denuder collection module 120 and particulate filter pack 150. It then flows through the acid gas scrubber 160 to the analyzer 114. During the sampling phase, the analyzer 114 determines the level of gaseous elemental mercury vapour.

The air flow through the denuder 120 is switched to a desorbing flow by actuating valves, as valves 56 and 76 in the first embodiment. In desorbing mode these valves serve to eliminate the gaseous flow from the stack by introducing a zero air flow upstream from the denuder. In the desorption phase, the particulate filter trap 150 is first desorbed. First, the pyrolyser 152 is actuated, to ensure breakdown of any mercury compounds that may pass through. Once the pyrolyser 152 has reached its full operating temperature, the heater 154 around the particulate filter pack 150 itself is actuated, to desorb mercury from the filter pack 150. Initially, a significant quantity of mercury compounds may be given off, which will be broken down by the pyrolyser 152. Once the heater 154 reaches its full operating temperature, the fraction of mercury compounds being desorbed will drop significantly.

In any event, pure gaseous elemental mercury will be passed to the analyzer 114 for measurement. With the particulate filter pack 150 completely desorbed and cleaned, the pyrolyser 152 and heater 154 can be left actuated. Then, the quartz denuder 120 is desorbed, by actuating its heating element 128. Again, the desorbed mercury vapour is detected by the analyzer 114 measurement.

With all the measurements completed, the individual components have cooled down, with fans and the flow of zero air. Once the temperature drops sufficiently, then the device switches back to a fresh sampling cycle, by actuating valves, as valves 56 and 76 of the first embodiment.

Figure 3:
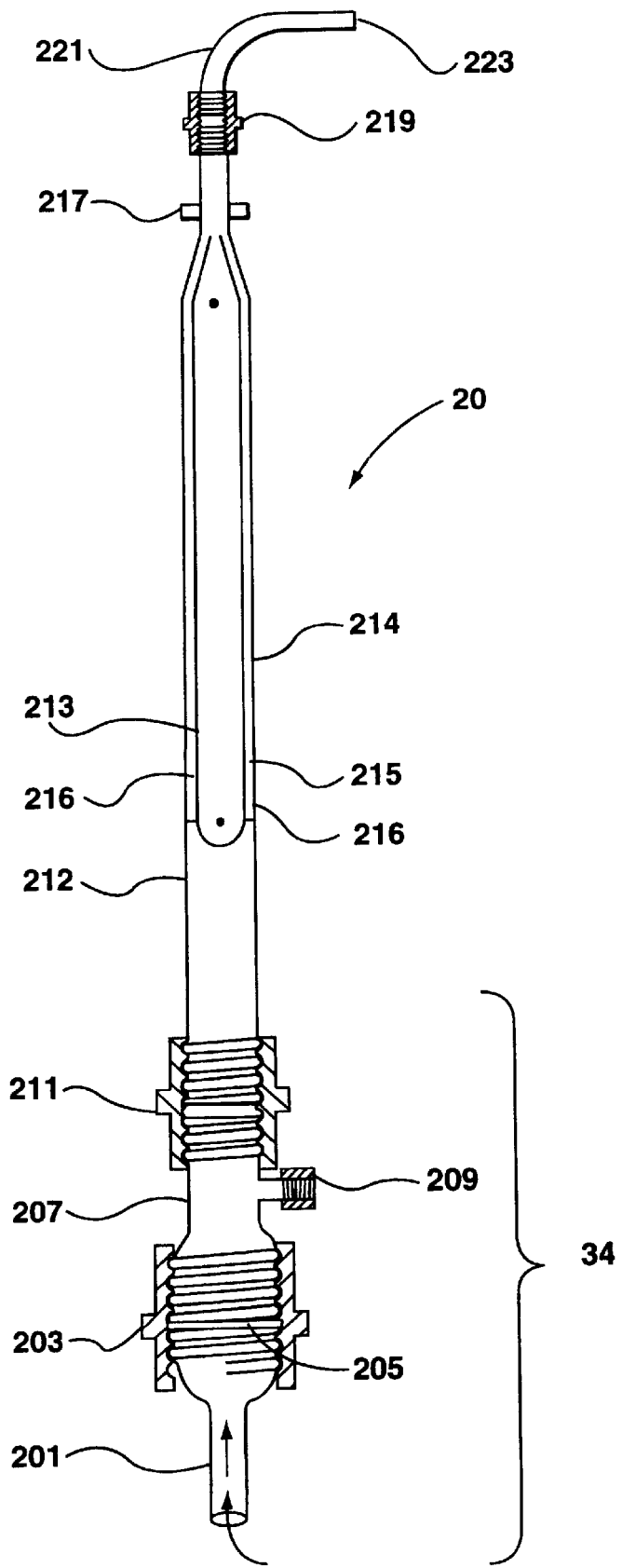
FIG. 3 is a plan view of the denuder of the present invention.

Referring now to FIG. 3, a plan view of the denuder 20 of the present invention, denuder 20 comprises four different segments 201, 207, 212 and 221 connected by couplers 203, 211, and 219 with screw connections in known manner. An impactor coupler 203 provided with an impact plate 205 connects an intake tube 201 to a t-adaptor section 207. A denuder coupler 211 connects the t-adaptor section 207 to a denuder section 212. An outlet coupler 219 connects the denuder section 212 to a 90° adapter 221.

The inlet 34 comprises the intake tube 201, the impactor coupler 203 with impact plate 205, t-adaptor section 207, a t-connector 209, and the denuder coupler 211. Downstream from inlet 34 the denuder section 212 comprises an inner hollow cylindrical element 213, and an outer cylindrical element 214, which together define an annular gap 215. The surfaces of elements 213, 214 bonding the annular gap 215 are etched and coated (see below) with a selected coating, indicated at 216. The hollow inner element 213 is provided with a vent in its downstream end, to enable it to allow pressure equalization during heating and cooling. Further downstream at the terminus of collecting surface 213 is a stop glass 217. Stop glass 217 serves to mount denuder 20 in a fixed vertical position within a tight fitting tube 21 (see FIG. 1). Further downstream from stop glass 217 is located outlet coupler 219 which serves to connect the outer cylindrical element 214 to a downstream terminus of 90° adapter 221 with an outlet port 223. The outlet port 223 extends at 90° from the vertical position of the denuder 20 and is connected to the sample line 40.

In use, ambient air flows into denuder 20 via intake tube 201. The air flow contacts the impact plate 205. As the air flow passes through the impactor coupler 203, larger particles hit the plate 205 and adhere. Such impactor plates are well known in the art and may include various surface coatings to ensure that larger particles are retained on the plate. Smaller particles entrained in the air flow are free to pass around the periphery of the plate thus continuing downstream toward the collecting surface.

The construction of intake tube 201 is well known to those skilled in the art. The preferred embodiment of intake tube 201 is such that with the impactor plate 205 in coupler 203, the intake tube 201 is described as an elutriator with an acceleration jet of 10 1 pm with a 2.5 micron cut. This means that with an air flow of ten litres per minute, particles of 2.5 microns or greater will be removed by the impactor. Cut off typically can be set in the range 2.5 to 10 microns.

The t-adaptor section 207 includes the t-connector 209 which in the preferred embodiment is a one quarter inch compression fitting which allows zero air to be introduced into the denuder 20. The use of t-connector 209 to introduce zero air eliminates the need for a valve upstream of the denuder 20; in the desorption cycle, zero air flowing through t-connector 209 will displace any ambient air entering through intake tube 201, hence closing off the denuder 20 to the exterior.

The denuder coupler 211 connects t-adaptor section 207 to denuder section 212 which contains the collecting surface 216. As described, in the preferred embodiment, the denuder 20 is an annular denuder in that the collecting surface 216 surrounds an annular gap on space 215.

The annular space 215 is important as denuders work by diffusion under laminar flow conditions. Thus, the small annular space 215 allows for efficient removal of RGM from the air flow passing through the denuder.

If the diffusion coefficient of the analyte is known, the flow through the denuder is laminar, and the flow rate is known, the efficiency with which a given length denuder can remove a substance can be calculated. A simple tubular denuder capable of removing RGM at 10 LPM would have to be quite long (>90 cm) and this would be difficult to heat and cool quickly. An equivalent annular denuder would need to be only about 6" long. Here, the denuder has the following dimensions: 380 mm long, 22 mm OD, 18 mm id of the outer glass (element 214), and 16 mm OD of the inner elements. (This gives a 1 mm air gap for the annulus (ring) (element 215) between the outer & inner surfaces); the collecting surface 216 is approximately 250 mm long. The denuder 20 is longer for several reasons, namely: a pre-heat region is provided upstream of the annular gap 215 in order to allow the zero air to preheat; a large amount of extra surface area is provided, in case part of the active area becomes passivated by other compounds in the air.

While the quartz denuder 20 and 120 have been described as being coated with potassium chloride, other types of salts and mixtures will also work, although the degree of effectiveness may well vary from one sort to another. Thus, it may be possible to use sodium chloride or a combination of potassium chloride and soda lime.

It has been found that the quartz denuder 20 will last for a matter of weeks before it needs to recoated, when used continuously. The following is coating technique that was developed during the laboratory testing KCl, but is noted that other methods may provide equal or better results. The method is as follows, (1) The denuder 20 is rinsed using high quality DI (deionised) water. It is essential to remove all traces of KCl, and the denuder is agitated while it is full with water to accelerate the cleaning process;

(2) The denuder 20 is rinsed with high quality methanol, and allowed to dry. Zero air or argon can be blown through the denuder 20 to speed the drying process;

(3) A super saturated KCl solution is prepared by, heating 75 ml of clean DI water in a clean beaker to approximately 50° C.; adding high purity, mercury free KCl, and mixing vigorously until no more KCl will dissolve in the solution; and allowing the solution to stand while tilting the beaker to ensure that the crystals collect in one corner of the beaker (to reduce residual mercury levels in the solution, the KCl can be heated in a ruffle furnace at 600° C. for two hours to drive off the mercury, and the solution can be purged wit zero air or argon before use).

(4) Using rubber tubing, to provide a connection to a rubber bulb or other easily controlled source of vacuum, the solution is drawn into the quartz denuder 20; to do this the outlet of the quartz denuder 20 is dipped into the beaker with the side away from pool of undissolved crystals and the solution is slowly drawn from the beaker up the entire active length of the denuder 20, with the solution not being drawn above the frosted portion of the denuder;

(5) The solution is held in the denuder for one minute, and then drained slowly;

(6) The denuder 20 is dried with air or argon;

(7) The denuder 20 is inspected to ensure that a smooth even coating or material has been deposited and if not, the previous three steps are repeated.

(8) All traces of KCl are removed from the outlet of the denuder 20 by dipping into a source of DI water and immersing to the appropriate depth, and repeating at least 3 times, with a fresh supply of water for each rinse operation;

(9) Again zero air or argon is used to dry the denuder 20;

This is but one method for coating the denuder. Less concentrated solutions of the adsorbent solution have been demonstrated to work as well.

Although the preferred embodiment may use an annular denuder as an adsorber, any adsorber capable of thermal regeneration such as a tubular denuder, or conventional packed cartridge may be substituted for the denuder. Adsorbent cartridges are well known and may be made of a wide variety of materials (glass, ceramic) and have wide variety of internal materials and forms for holding the adsorbent coating. (eg: quartz or ceramic, chips or beads). Also conventional ceramic honeycomb style catalytic carriers may be used. The only requirements are that the material itself not retain mercury, and that they withstand high temperatures.

It is preferred for the coating in the denuder or adsorption unit to be such as to release the mercury or elemental mercury on desorption, and the inventor's experience has been that this is always the case. However, for some coating materials and possibly some operating conditions, at least a portion of the mercury might be released as reactive gaseous mercury. In such a case, a pyrolysis unit can be provided immediately downstream, for pyrolysing the released RGM to elemental mercury.

We claim:

1. A speciation module for repeated speciation of reactive gaseous mercury from elemental mercury and particulate bound mercury and for use with mercury analysis equipment, the speciation module comprising:

an adsorption unit having an extended transfer surface and a coating including a halogen salt on the transfer surface for adsorbing reactive gaseous mercury and allowing elemental mercury and particulate bound mercury to pass through the adsorption unit, the adsorption unit having an adsorption unit inlet opening directly to a gas sample and an adsorption unit outlet for connection to a pump means, for drawing the gas sample through the adsorption unit, and being formed of a material capable of withstanding a desorption temperature;

a first inlet for a flushing gas, substantially free of mercury vapour, for flushing out of the adsorption unit and connectable to the adsorption unit inlet;

a heating means for heating the adsorption unit to the desorption temperature higher than an adsorption temperature, the desorption temperature being such as to cause reactive gaseous mercury adsorbed onto the coating to be released as gaseous elemental mercury vapour, for measurement, and such as to regenerate the coating on the transfer surface to facilitate repeated speciation; and, a temperature controller for controlling the heating means, whereby the adsorption unit can be maintained at the adsorption temperature for adsorption of the reactive gaseous mercury and, at the desorption temperature for desorption of the reactive gaseous mercury as gaseous elemental mercury vapour.

2. A detection module as claimed in claim 1, wherein the heating means includes a first heating element located around the adsorption unit and a first heating controller connected to the first heating element, the first heating controller being capable of regulating the temperature of the first heating element to a first temperature at which the adsorption unit functions to adsorb the reactive gaseous mercury, and to a second, elevated temperature at which reactive gaseous mercury compounds adsorbed on the adsorption unit break down and release mercury as gaseous elemental mercury vapour.

3. A detection module as claimed in claim 2, which includes a detection module housing, in which the adsorption unit is mounted with the adsorption unit inlet extending out of the detection module housing, and wherein the heating means includes a second heating element located around the adsorption unit inlet and a second heater controller connected to the second heating element, for maintaining the adsorption unit inlet at a set temperature.

4. A detection module as claimed in claim 3, wherein the heating means includes a third heating element within the detection module housing for heating the housing and a third heating element controller for control thereof.

5. A detection module as claimed in claim 4, which includes a first fan for cooling the adsorption unit and a second fan for blowing air through the detection module housing for cooling thereof.

6. A detection module as claimed in claim 1, which includes at least one fan for cooling the adsorption unit.

7. A detection module as claimed in claim 1, wherein the adsorption unit comprises a denuder and wherein the adsorption unit includes a first outlet for connection to the pump means and a particulate filter pack located between the adsorption unit outlet and the first outlet.

8. A detection module as claimed in claim 7, wherein the filter pack comprises filter material capable of being subjected to elevated temperature to release mercury vapour and to regenerate the filter pack for repeated speciation, whereby the particulate bound mercury collected in the particulate filter pack can be released as elemental mercury vapour by heating the filter material.

9. A speciation module as claimed in claim 8, wherein the adsorporation unit inlet includes an impactor for trapping particles greater than a predetermined size.

10. detection module as claimed in claim 1, which includes an inlet T-shaped connector connected to the adsorption unit inlet, the inlet T-shaped connector providing a straight through connection for the gas sample and a side connection connected to the first inlet for supply of flushing gas.

11. A detection module as claimed in claim 10, which includes a first valve having a first connection port connected to the first inlet, a first valve outlet and a second valve outlet, with the side connection of the T-shaped connector connected to the second valve outlet, and a flow restrictor connected to the first valve outlet, whereby the first valve can selectively connect the first inlet to either the flow restrictor for enabling a restricted flow of flushing gas vent to atmosphere or to the adsorption unit through the T-shaped connector for supply of flushing gas.

12. A speciation module as claimed in claim 1, wherein the coating comprises one of potassium chloride, sodium chloride and a combination of potassium chloride and other halogen salts.

13. A selection module as claimed in claim 1 or 12, wherein the denuder is formed from quartz glass.

14. A speciation module as claimed in claim 1, wherein the adsorption unit inlet includes an impactor for trapping particles greater than a predetermined size.

15. An apparatus for use with a mercury analyzer for the repeated speciation of reactive gaseous mercury, the apparatus comprising:
   (1) an adsorption unit having an extended surface and a coating a halogen salt on the extended surface for adsorbing reactive gaseous mercury and allowing elemental mercury and particulate bound mercury to pass through the adsorption unit, the adsorption unit having an adsorption unit inlet opening directly to a gas sample and an adsorption unit outlet and being formed of a material capable of withstanding a desorption temperature;
   (2) a heating means for heating the adsorption unit to the desorption temperature higher than an adsorption temperature, the desorption temperature being such as to cause reactive gaseous mercury adsorbed on the coating to be desorbed and vaporized as elemental mercury vapour and such as to cause the coating on the extended surface to regenerate to facilitate repeated measurements;
   (3) a temperature controller for controlling the heating means, whereby the adsorption unit can be maintained at the adsorption temperature for adsorption of the reactive gaseous mercury and, at the desorption temperature for desorption;
   (4) a pump means connected to the adsorption unit outlet for drawing the gas sample through the adsorption unit; and,
   (5) a flushing gas supply means for supply of a flushing gas and connectable to the adsorption unit inlet, for passing flushing gas through the adsorption unit, whereby in use, the gas sample is drawn through the adsorption unit by the pump means in a sampling phase and reactive gaseous mercury is adsorbed onto the coating of the adsorption unit, and in a desorption phase, the heating means is actuated and flushing gas is passed through the adsorption unit from the adsorption unit inlet to the adsorption unit outlet so that adsorbed reactive gaseous mercury is desorbed as elemental mercury vapor-and entrained in the flushing gas flow.

16. An apparatus as claimed in claim 15, wherein the flushing gas supply means is integral with the pump means and is connected to the adsorption unit inlet by a flushing gas supply line.

17. An apparatus as claimed in claim 16, wherein the pump means is connected to the adsorption unit outlet by a sample line, and wherein the sample line includes a branch connection port for connection to a mercury analyzer.

18. An apparatus as claimed in claim 17, wherein the sample line and the flushing connection line are provided with a common line heater and a line heater controller.

19. An apparatus as claimed in claim 18, which includes a first valve having a first connection port, a first valve outlet and a second valve outlet, the valve being provided in the flushing gas supply line and being operable to connect the first connection port to either one of the first and second valve outlets, with the first connection port and the first valve outlet being connected in the flushing gas supply line.

20. An apparatus as claimed in claim 19, which includes a T-shaped connector connected to the adsorption unit inlet, the T-shaped connector providing a straight through connection for the gas sample into the adsorption unit and including a side connection port connected to the flushing gas supply line.

21. An apparatus as claimed in claim 20, which includes a flow restrictor connected to the second valve outlet of the first valve, the first valve connecting the flushing gas sample line to the flow restrictor during a sampling phase of the adsorption unit, whereby a restricted flow of flushing gas is permitted through the flushing gas supply line, so that possible back flow of contaminants up the flushing gas supply line is prevented.

22. An apparatus as claimed in claim 21, which includes a filter means, comprising at least one of a final filter and a particulate filter pack located in the flushing gas supply line immediately upstream of the first valve means.

23. An apparatus as claimed in claim 22, wherein the adsorption unit is mounted in an adsorption unit housing, and wherein the heating means comprises a first heating element located around the adsorption unit for heating thereof, a first heating element controller connected to the first heating element, the heating element controller being capable of maintaining the first heating element at a first temperature during the sampling phase and at a second, elevated temperature during the desorption phase, and wherein the adsorption unit housing includes a housing heater and a housing heater controller for control thereof, to maintain the adsorption unit housing at a desired temperature.

24. An apparatus as claimed in claim 23, which includes an inlet heater around the T-shaped connector, and an inlet heating controller for maintaining the inlet at a desired temperature.

25. An apparatus as claimed in claim 21, which includes a second valve including a second connection port and first and second inlet ports, the second valve being operable to connect the second connection port to either one of the first and second inlet ports, the second connection port and the first outlet port being connected in the sample line between the adsorption unit and the pump means, and wherein the apparatus includes an air inlet and a first stage scrubber provided between the air inlet and the second inlet port, whereby the second valve provides a connection between the second connection port and the first inlet port during the sampling phase, for drawing a sample gas through the adsorption unit, and during a desorption phase, the second connection port is connected to the second port so that the pump means draws air through the first stage scrubber for generation of flushing gas.

26. An apparatus as claimed in claim 25, wherein the pump means comprises a sample pump having a pump inlet connected to the second connection port of the second valve and a pump outlet, and wherein a second stage scrubber is connected between the pump outlet and the flushing gas supply line.

27. An apparatus as claimed in claim 26, which includes a pressure relief valve connected to the pump outlet, for maintaining a desired pressure in the flushing gas supply line.

28. An apparatus as claimed in claim 27, which includes a mass flow meter and a buffer tank connected between the second valve and the pump.

29. An apparatus as claimed in claim 16, in combination with a mercury analyzer, wherein the mercury analyzer is connected to the branch connection port of the sample line and to the flushing gas supply line, and wherein the combination includes a controller connected to the pumping means, the heating means and the mercury analyzer, for control thereof.

30. An apparatus as claimed in claim 15, which includes a particulate filter pack connected between the pump means and the adsorption unit outlet and located adjacent the adsorption unit outlet, for trapping particles having mercury bound thereto and passing the elemental mercury therethrough.

31. An apparatus as claimed in claim 30, wherein the particulate filter pack is regeneratable to facilitate repeated measurements, and includes means for heating the regeneratable filter pack, to desorb mercury from particles trapped therein.

32. An apparatus as claimed in claim 31, wherein the regeneratable filter pack includes a filter core and a filter heater located around the core for heating the core to cause desorption of mercury, and a pyrolysis device downstream from the filter core for pyrolysing any mercury desorbed from the filter pack as a mercury compound, whereby any mercury compounds are pyrolysed to gaseous elemental mercury vapour.

33. An apparatus as claimed in claim 31, wherein the adsorption unit inlet includes an impactor for trapping particles greater than a predetermined size.

34. An apparatus as claimed in claim 15, wherein the apparatus further comprises a cooling means for cooling the absorption unit, whereby a new measurement cycle may begin.

35. An apparatus as claimed in claim 15, wherein the adsorption unit inlet includes an impactor for trapping particles greater than a predetermined size.

36. A method for speciation of reactive gaseous mercury from elemental mercury and particulate bound mercury in a gas sample and measurement of the reactive gaseous mercury, the method comprising the steps of:

(1) passing the gas sample through an adsorption unit having an adsorption unit inlet opening directly to the gas sample and an adsorption unit outlet and being capable of withstanding a desorption temperature, said adsorption unit having an extended surface provided with a coating for adsorbing reactive gaseous mercury and allowing the elemental mercury and the particulate bound mercury in the gas sample to pass through the adsorption unit, the adsorption unit being maintained at a suitable adsorption temperature above ambient temperature of the gas sample to prevent condensation of water vapour during adsorption;

(2) after a known quantity of the gas sample has been passed through the adsorption unit, terminating supply of the gas sample, and passing a flushing gas through the adsorption unit; and (3) while passing the flushing gas through the adsorption unit, heating the adsorption unit to the desorption temperature higher than the adsorption temperature, to cause desorption of reactive gaseous mercury compounds as gaseous elemental mercury vapour for entrainment in the flushing gas and to regenerate the coating of the adsorption unit to facilitate repeated mercury speciation without significantly compromising the coating, and passing the flushing gas with the entrained gaseous elemental mercury vapour to a mercury analyzer for determination of the level of the reactive gaseous mercury in the gas sample.

37. A method as claimed in claim 36, which includes heating the adsorption unit in step (3) to a temperature of substantially 500° C.

38. A method as claimed in claim 37, which includes maintaining an adsorption temperature of substantially 50°.

39. A method as claimed in claim 38, which includes passing the gas sample into the adsorption unit through an inlet, maintaining the inlet at a first, lower temperature for adsorption and a second, higher temperature for desorption.

40. A method as claimed in claim 39, which includes maintaining the inlet at a temperature of substantially 50° C. for adsorption and substantially 90° C. for desorption.

41. A method as claimed in claim 36, which further comprises the step of:

(4) passing a portion of the gas sample that has passed through the adsorption unit to the mercury analyzer prior to step (2), for determination of the level of elemental mercury in the gas sample.

42. A method as claimed in claim 41, which includes providing a denuder as the adsorption unit and filtering out particles containing particulate mercury from the gas sample, downstream from the denuder while allowing the elemental mercury in the gas sample to pass therethrough.

43. A method as claimed in claim 42, which further comprises the step of:

(5) filtering out particles with a regeneratable filter pack, and prior to step (3) and after step (4), heating the regeneratable filter pack to a temperature where the particulate bound mercury is desorbed from the regeneratable filter pack as gaseous elemental mercury vapour, and entraining that gaseous elemental mercury vapour in the flushing gas flow, for determination of the level of the particulate bound mercury in the gas sample.

44. A method as claimed in claim 43, wherein, heating of the particulate filter pack comprises:

providing a pyrolysis means downstream from the filter pack and first heating the pyrolysis means to operating temperature, to ensure pyrolysis of any mercury compounds desorbed from the filter pack; and after the pyrolysis means has reached said operating temperature, maintaining the operating temperature on the pyrolysis means and heating the filter pack to cause mercury and mercury compounds to vaporize therefrom.

45. A method as claimed in claim 44, wherein, after the mercury compounds on the regeneratable filter pack have been desorbed, maintaining the temperatures applied to the regeneratable filter pack and the pyrolysis means, and heating the denuder according to step (3) to desorb gaseous elemental mercury vapour therefrom, whereby mercury vapour from the denuder passes through the regeneratable filter pack for analysis.

46. A method as claimed in claim 45, which includes providing the absorption unit with a cooling means for cooling the absorption unit after step (3), whereby speciation of a new sample may begin.

47. A method as claimed in claim 36, which includes providing the adsorption unit in a separate detection module, and mounting the detection module externally and remotely from pumping means for drawing ambient air through the adsorption unit and providing flushing gas to the adsorption unit and remotely from the mercury analyzer.

48. A method as claimed in claim 47, which includes providing a pumping module including a pump for drawing the gas sample through the adsorption unit and means for generating flushing gas substantially free from mercury vapour, and providing a sample connection line and a flushing gas line between the pumping means and the collection module.

49. A method as claimed in claim 36, which includes providing a T inlet connector for the adsorption unit, providing a straight through connection to the adsorption unit for the sample gas and a branch connection for flushing gas, and during step (1) providing no flushing gas to the T inlet connector, whereby only the sample gas is drawn through the T inlet connector and into the adsorption unit, and in step (2) and (3) providing a flow of flushing gas to the T inlet connector substantially in excess of the flushing gas flow through the adsorption unit, whereby excess flushing gas vents to the exterior through the T inlet connector, to prevent contamination of the flushing gas flow through the adsorption unit from the exterior.

50. A method for repeated speciation of reactive gaseous mercury from elemental mercury and particulate bound mercury in a gas sample and measurement of the reactive gaseous mercury, the method comprising the steps of:

(1) passing the gas sample through an adsorption unit having an adsorption unit inlet opening directly to the gas sample and an adsorption unit outlet, said adsorption unit having an extended surface provided with a coating of ionic salt for adsorbing reactive gaseous mercury and allowing the elemental mercury and the particulate bound mercury in the gas sample to pass therethrough, the adsorption unit being maintained at a suitable adsorption temperature above ambient temperature of the gas sample to prevent condensation of water vapour during adsorption;

(2) after a known quantity of the gas sample has been passed through the adsorption unit, terminating supply of the gas sample, and passing a flushing gas through the adsorption unit; and (3) while passing the flushing gas through the adsorption unit, heating the adsorption unit to a suitable desorption temperature to cause desorption of reactive gaseous mercury compounds as gaseous elemental mercury vapour for entrainment in the flushing gas and thereby to regenerate the coating of the adsorption unit to facilitate repeated mercury speciation, and passing the flushing gas with the entrained gaseous elemental mercury vapour to a mercury analyzer for determination of the level of the reactive gaseous mercury in the gas sample.

* * * * *

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Title page,
Item [57], ABSTRACT,
Lines 5-8, "After collection of a sample, the coating it is heated to desorb the mercury as elemental gaseous mercury, which can then be detected and measured in conventional analyzer." has been changed to -- After collection of a sample, the coating is heated to desorb the mercury as elemental gaseous mercury, which can then be detected and measured in a conventional analyzer. --

Lines 15-17, the sentence "The pump module can be configured to a past the gas sample through scrubbers, to generate zero air as a flushing gas." has been changed to -- The pump module can be configured to generate zero air as a flushing gas. --

Column 1,
Line 45, "atomsphere 6-12 months" has been changed to -- atmosphere of 6-12 months --.
Line 65, the word "old-coated" has been changed to -- gold-coated --.

Column 2,
Line 43, quotations have been placed around -- Application of the Diffusion Screen Technique to the Determination of Gaseous Mercury and Mercury (II) Chloride in Flue Gases --.
Line 48, quotations have been placed around -- On the measurement of Volatile Metal Species at Elevated Temperatures --.

Column 3,
Line 55, the word "or", has been changed to -- of --.
Line 62, the paragraph "In accordance with a first aspect of the present invention, there is provided a detection module, for detecting airborne reactive gaseous mercury and for use with mercury analysis equipment, the detection module comprising:" has been changed to -- In accordance with a first aspect of the present invention, there is provided a speciation module, for repeated speciation of reactive gaseous mercury from elemental mercury and particulate bound mercury and for use with mercury analysis equipment, the speciation module comprising: --.

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Column 3 cont'd,
Line 65, the paragraph "an adsorption unit having an extended transfer surface and a coating on the transfer surface for adsorbing reactive gaseous mercury from a gas passing through the adsorption unit, the adsorption unit having an adsorption unit inlet opening directly to a gas sample containing reactive gaseous mercury and an adsorption unit outlet for connection to a pump means, for drawing the gas sample through the adsorption unit;" has been changed to -- an adsorption unit having an extended transfer surface and a coating including a halogen salt on the transfer surface for adsorbing reactive gaseous mercury and allowing elemental mercury and particulate bound mercury to pass through the adsorption unit, the adsorption unit having an adsorption unit inlet opening directly to a gas sample and an adsorption unit outlet for connection to a pump means, for drawing the gas sample through the adsorption unit, and being formed of a material capable of withstanding a desorption temperature; --.

Column 4,
Line 9, the paragraph "a heating means for heating the adsorption unit to a suitable desorption temperature higher than an adsorption temperature to cause reactive gaseous mercury adsorbed onto the coating to be released as gaseous elemental mercury vapour, for measurement; and" has been changed to -- a heating means for heating the adsorption unit to the desorption temperature higher than an adsorption temperature, the desorption temperature being such as to cause reactive gaseous mercury adsorbed onto the coating to be released as gaseous elemental mercury vapour, for measurement, and such as to regenerate the coating on the transfer surface to facilitate repeated speciation; and, --.
Line 18, the line "tion of elemental mercury" has been changed to -- tion of the reactive gaseous mercury as gaseous elemental mercury vapour. --.
Lines 38, 40, 46 and 51, the word "detection" has been changed to -- speciation --.
Line 59, the word "independably" has been changed to -- independently --.

Column 5,
Line 15, -- halogen -- has been inserted before "salt".
Line 18, the sentence "Another aspect of the present invention provides an apparatus for the detection of reactive gaseous mercury, the apparatus comprising:" has been changed to -- Another aspect of the present invention provides an apparatus for use with a mercury analyzer for the repeated speciation of reactive gaseous mercury, the apparatus comprising: --.
Line 22, the word "ionic" has been changed to -- halogen --.

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Column 5 cont'd,
Line 23, the line "ing reactive gaseous mercury, the adsorption unit hav-" has been changed to -- ing reactive gaseous mercury and allowing elemental mercury and particulate bound mercury to pass through the adsorption unit, the adsorption unit hav- --.
Line 24, the word "sample" has been deleted.
Line 25, the line "gas and an adsorption unit outlet;" has been changed to -- gas sample and an adsorption unit outlet and being formed of a material capable of withstanding a desorption temperature; --.
Line 26, the sentence "a heating means for heating the adsorption unit to a suitable desorption temperature higher than an adsorption temperature to cause gaseous reactive mercury adsorbed on the coating to be desorbed and vaporized as elemental mercury;" has been changed to -- a heating means for heating the adsorption unit to the desorption temperature higher than an adsorption temperature, the desorption temperature being such as to cause reactive gaseous mercury adsorbed on the coating to be desorbed and vaporized as elemental mercury vapour and such as to cause the coating on the extended surface to regenerate to facilitate repeated measurements; --.
Line 37, the word "a" be changed to -- the --.
Line 42, the words "a sample gas" has been changed to -- the gas sample --.
Line 49, the line "reactive gaseous mercury is desorbed, vaporized and" has been changed to -- reactive gaseous mercury is desorbed as elemental mercury vapor, and --.
Line 66, the sentence "Another aspect of the present invention provides a method for determining the quantity of reactive gaseous mercury in a gas, the method comprising the steps of:", has been changed to -- Another aspect of the present invention provides a method for speciation of reactive gaseous mercury from elemental mercury and particulate bound mercury in a gas sample and measurement of the reactive gaseous mercury, the method comprising the steps of: --.

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Column 6,
Line 1, the sentence "(1) passing a gas sample through an adsorption unit having an adsorption unit inlet opening directly to a gas sample and an adsorption unit outlet, said adsorption unit having an extended surface provided with a coating for adsorbing reactive gaseous mercury and being maintained at a suitable adsorption temperature above ambient temperature of the gas sample to prevent condensation of water vapour during adsorption;" has been changed to -- (1) passing the gas sample through an adsorption unit having an adsorption unit inlet opening directly to the gas sample and an adsorption unit outlet and being capable of withstanding a desorption temperature, said adsorption unit having an extended surface provided with a coating for adsorbing reactive gaseous mercury and allowing the elemental mercury and the particulate bound mercury in the gas sample to pass through the adsorption unit, the adsorption unit being maintained at a suitable adsorption temperature above ambient temperature of the gas sample to prevent condensation of water vapour during adsorption; --.

Line 9, the sentence "(2) after a known quantity of gas has been passed through the adsorption unit, terminating supply of the sampled gas, and passing a flushing gas through the adsorption unit; and" has been changed to -- (2) after a known quantity of the gas sample has been passed through the adsorption unit, terminating supply of the gas sample, and passing a flushing gas through the adsorption unit; and --.

Line 13, the sentence "(3) while passing the flushing gas through the adsorption unit, heating the adsorption unit to a suitable desorption temperature higher than the desorption temperature to cause desorption of reactive gaseous mercury compounds as gaseous elemental mercury vapour for entrainment in the flushing gas, and passing the flushing gas with the entrained gaseous elemental mercury vapour to a mercury analyzer." has been changed to -- (3) while passing the flushing gas through the adsorption unit, heating the adsorption unit to the desorption temperature higher than the adsorption temperature, to cause desorption of reactive gaseous mercury compounds as gaseous elemental mercury vapour for entrainment in the flushing gas and to regenerate the coating of the adsorption unit to facilitate repeated mercury speciation without significantly compromising the coating, and passing the flushing gas with the entrained gaseous elemental mercury vapour to a mercury analyzer for determination of the level of the reactive gaseous mercury in the gas sample. --.
Line 35, the word "in" has been deleted.
Line 65, the word "detection" has been changed to -- speciation --.

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Column 7,
Line 5, the line "Tekran Inc. These components 12, 14 and 18 are also" has been changed to -- Tekran Inc. The analyzer 14 is also --.
Line 30, the word "detection" has been changed to -- speciation --.

Column 8,
Line 3, -- be -- has been inserted after "to".
Line 12, the word "he" has been changed to -- be --.
Line 25, the ":" has been deleted.

Column 9,
Line 17, -- the -- has been inserted after "to".
Line 27, the word "detection" has been changed to -- speciation --.
Line 35, -- of -- has been inserted after "amount".
Line 37, the line "set to a temperature 500°C. For the external temperature" has been changed to -- set to a temperature of 500°C, a temperature low enough that it does not significantly compromise the denuder coating. For the external temperature --.
Line 40, "slight" has been replaced with -- slightly --.
Line 41, -- a -- has been inserted after "at".
Line 58, "pump module 16" has been changed to -- pump module 12 --.
Line 65, the word "recalabrate" has been changed to -- recalibrate --.

Column 10,
Line 2, the word "programable" has been changed to -- programmable --.
Line 4, the word "detection" has been changed to -- speciation --.
Line 5, -- be -- has been inserted after "to".
Line 7, the words "out gas" have been changed to -- emit gaseous --.
Line 37, the line "through the restrictor 64, this is to maintain a steady, forward" has been changed to -- through the restrictor 64. This is to maintain a steady, forward --.
Line 60, -- it -- has been inserted after "that".

Column 11,
Line 10, the words "is places" has been changed to -- displaces --.
Line 11, the word "nalyzer" has been changed to -- analyzer --.
Line 32, -- the -- has been inserted after "that".

Column 12,
Line 20, the word "fitter" has been changed to -- filter --.
Line 41, the words "concentration is" has been changed to -- concentrations --.
Line 45, the word "a" has been changed to -- an --.

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Column 13,
Lines 50 and 67, the word "adapter" has been changed to -- adaptor --.
Line 57, the word "bonding" has been changed to -- bounding --.

Column 14,
Line 17, the words "10 1 pm" has been changed to -- 10 lpm --.
Line 44, the word "LPM" has been changed to -- lpm --.
Line 48, the word "id" has been changed to -- ID --.
Line 61, the word "sort" has been changed to -- salt --.
Line 62, the line "may be possible to use sodium chloride or a combination of has been changed to -- may be possible to use other halogen salts, such as sodium chloride or a combination of --.
Line 63, the words "soda lime" has been changed to -- other salts --.
Line 65, -- be -- has been inserted after "to".
Line 66, -- a -- has been inserted after "is".

Column 15,
Line 10, the "," has been deleted.
Line 17, the word "ruffle" has been changed to -- muffle --.
Line 19, the word "wit" has been changed to -- with --.
Line 20, the "." has been changed to a -- ; --.
Line 34, the word "or" has been changed to -- of --.
Line 35, the "." has been changed to -- ; --.
Line 41, the ";" has been changed to -- . --.
Line 52, the first "." has been removed.

Column 17,
Line 6, the word "adsorportion" has been changed to -- adsorption --.
Line 8, the word -- A -- has been inserted before "detection".
Line 21, the word -- to -- has been inserted before "vent".
Line 28, the word "selection" has been changed to -- speciation --.
Line 36, the word "a" has been deleted.

Column 18,
Line 6, the word "vapor-and" has been changed to -- vapor and --.

Column 19,
Line 53, the word "absorption" has been changed to -- adsorption --.

UNITED STATES PATENT AND TRADEMARK OFFICE
CERTIFICATE OF CORRECTION

PATENT NO.    : 6,475,802 B2
DATED         : November 5, 2002
INVENTOR(S)   : Schaedlich et al.

It is certified that error appears in the above-identified patent and that said Letters Patent is hereby corrected as shown below:

Column 20,
Line 27, -- C -- has been inserted after "50º".

Column 21,
Lines 10 and 11, the word "absorption" has been changed to -- adsorption --.

Column 22,
Line 15, the word "absorption" has been changed to -- adsorption --.

Signed and Sealed this

Eighth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,475,802 B2
DATED : November 5, 2002
INVENTOR(S) : Schaedlich et al.

It is certified that error appears in the above-identified patent and that said Letters Patent is hereby corrected as shown below:

Column 16,
Lines 31, 42, 43, 45, 50, 52, 54, 56, 58, 60 and 65, the word "detection" has been changed to -- speciation --.

Column 17,
Lines 8 and 14, the word "detection" has been changed to -- speciation --.

Signed and Sealed this

Twenty-sixth Day of August, 2003

JAMES E. ROGAN
*Director of the United States Patent and Trademark Office*